United States Patent
Lee et al.

(10) Patent No.: US 9,938,504 B2
(45) Date of Patent: Apr. 10, 2018

(54) METHOD FOR PRODUCING INDUCED PLURIPOTENT STEM CELL FROM MESENCHYMAL STEM CELL AND INDUCED PLURIPOTENT STEM CELL PRODUCED BY THE METHOD

(71) Applicant: BBHC CO., LTD., Seoul (KR)

(72) Inventors: Sang Yeon Lee, Gyeonggi-do (KR); Won Ju Jung, Seoul (KR); Ho Bin Kim, Seoul (KR); Min Sun Oh, Seoul (KR); Kye Ho Lee, Seoul (KR)

(73) Assignee: BBHC CO., LTD., Seoul (KR)

( * ) Notice: Subject to any disclaimer, the term of this patent is extended or adjusted under 35 U.S.C. 154(b) by 0 days.

(21) Appl. No.: 14/783,893

(22) PCT Filed: Nov. 1, 2013

(86) PCT No.: PCT/KR2013/009845
§ 371 (c)(1),
(2) Date: Oct. 12, 2015

(87) PCT Pub. No.: WO2015/064795
PCT Pub. Date: May 7, 2015

(65) Prior Publication Data
US 2016/0230146 A1    Aug. 11, 2016

(51) Int. Cl.
*C12N 5/07* (2010.01)
*C12N 5/074* (2010.01)

(52) U.S. Cl.
CPC ........ *C12N 5/0696* (2013.01); *C12N 2500/76* (2013.01); *C12N 2501/40* (2013.01); *C12N 2506/1369* (2013.01)

(58) Field of Classification Search
CPC .................. C12N 5/0696; C12N 2500/76
See application file for complete search history.

(56) References Cited

U.S. PATENT DOCUMENTS

| | | | |
|---|---|---|---|
| 8,673,633 B2 | 3/2014 | Park | |
| 2010/0135970 A1 | 6/2010 | Kishore et al. | |
| 2011/0256626 A1 | 10/2011 | Park | |
| 2016/0257935 A1 | 9/2016 | Lee et al. | |
| 2016/0257936 A1 | 9/2016 | Lee et al. | |
| 2016/0272936 A1 | 9/2016 | Lee et al. | |

(Continued)

FOREIGN PATENT DOCUMENTS

| KR | 10-2011-0032989 | 3/2011 |
|---|---|---|
| KR | 10-2013-077944 | 7/2013 |

OTHER PUBLICATIONS

International Search Report for PCT/KR2013/009845, dated Jul. 18, 2014, two pages.

(Continued)

*Primary Examiner* — Kara Johnson
(74) *Attorney, Agent, or Firm* — Nixon & Vanderhye P.C.

(57) ABSTRACT

The present invention relates to a medium composition containing an *Ecklonia cava* extract for dediffentiating an induced pluripotent stem cell. Also, the present invention relates to a method for producing induced pluripotent stem cells using the medium composition. When using the medium composition, according to the present invention, induced pluripotent stem cells using mesenchymal stem cells can be produced safely, easily, and efficiently, and the pluripotent stem cells which have been produced can be useful as a cell treatment agent by being capable of being differentiated into a variety of cells.

4 Claims, 3 Drawing Sheets

(56) References Cited

U.S. PATENT DOCUMENTS

| | | |
|---|---|---|
| 2016/0272939 A1 | 9/2016 | Lee et al. |
| 2016/0272942 A1 | 9/2016 | Lee et al. |
| 2017/0107481 A1 | 4/2017 | Lee et al. |
| 2017/0114328 A1 | 4/2017 | Lee et al. |

OTHER PUBLICATIONS

Ali et al., "Phlorotannin-incorporated mesenchylmal stem cells and their promising role in osteogenesis imperfect", *Journal of Medical Hypotheses and Ideas*, Jul. 2012, vol. 6, No. 2, pp. 85-89.

Communication and Supplementary European Search Report dated Feb. 22, 2017, issued in connection with European Patent Application No. 13 89 6647.8 ("Method for Producing Induced Pluripotent Stem Cell From Mesenchymal Stem Cell and Induced Pluripotent Stem Cell Produced by the Method" Lee et al., Nov. 1, 2013) (12 pages).

Kang et al, "Effect of Dieckol, a Component of *Ecklonia cava*, on the Promotion of Hair Growth", International Journal of Molecular Sciences, vol. 13, No. 12, May 23, 2012, pp. 6407-6423.

Lee et al, "Molecular characteristics and anti-inflammatory activity of the fucoidan extracted from *Ecklonia cava*", Carbohydrate Polymers, Applied Science Publishers, Ltd. Barking, GB, vol. 89, No. 2, Mar. 18, 2012, pp. 599-606.

Okita et al, "Induction of pluripotency by defined factors", Experimental Cell Reseach, vol. 316, No. 16, Oct. 1, 2010, pp. 2565-2570.

Liu et al, "n-Butylidenephthalide (BP) Maintains Stem Cell Pluripotency by Activating Jak2/Stat3 Pathway and Increases the Efficiency of iPS Cells Generation", PLOS One, vol. 7, No. 9, Sep. 7, 2012, p. 44024.

Wijesinghe et al, "Biological activities and potential cosmeceutical applications of bioactive components from brown seaweeds: a review", Phytochemistry Reviews, Kluwer Academic Publishers, DO, vol. 10, No. 3, Jun. 17, 2011, pp. 431-443.

Obokata et al, "Stimulus-triggered fate conversion of somatic cells into pluripotency", Nature, vol. 505, No. 7485, Jan. 29, 2014, pp. 641-647.

AmnioMAX™ C-100 and AmnioMAX™ II Complete Media, Gibco by Life Technologies™, 2013, Publication No. MAN0007317, Rev. 1.00 (2 pages).

Chang Medium® C with Gentamicin for Human Amniotic Fluid Cells, Catalog No. 99419, IrvineScientic® PN40819 Rev3 www.irvinesci.com/.../40819_Chang_C_w_Gent_99419_Rev3_WEB.pdf (42 pages) 2017.

Communication dated Mar. 10, 2017, issued in connection with European Patent Application No. 13 89 6647.8 ("Method for Producing Induced Pluripotent Stem Cell From Mesenchymal Stem Cell and Induced Pluripotent Stem Cell Produced by the Method" Lee et al., Nov. 1, 2013) (1 page).

Mesencult™—XF Medium, "Defined, xeno-free medium for human mesenchymal stem cells", Stemcell™ Technologies, 2017, Document #29919, Version 2-4-0 (2 pages).

U.S. Appl. No. 15/328,656 (Lee et al. "Method for Preparing Induced Pluripotent Stem Cell Line From Mesenchymal Stem Cells, and Cell Line Obtained Thereby" filed Jan. 24, 2017 as U.S. National Phase of PCT/KR2014/007207 (filed Aug. 5, 2014)).

METHOD FOR PRODUCING INDUCED PLURIPOTENT STEM CELL FROM MESENCHYMAL STEM CELL AND INDUCED PLURIPOTENT STEM CELL PRODUCED BY THE METHOD

This application is the U.S. national phase of International Application No. PCT/KR2013/009845 filed 1 Nov. 2013 which designated the U.S., the entire content of which is hereby incorporated by reference.

TECHNICAL FIELD

The present invention relates to medium compositions for inducing pluripotent stem cells from mesenchymal stem cells, and methods for producing induced pluripotent stem cells using the same.

BACKGROUND ART

Stem cells are a generic term for undifferentiated cells before differentiated stages, which can be obtained from various tissues. Stem cells have properties capable of continuously producing cells identical to themselves for a certain amount of time in an undifferentiated state, and properties capable of differentiating into various cells which constitute biological tissues, under proper conditions.

Stem cells can be broadly classified as embryonic stem cells and adult stem cells, according to differentiation potency and generating stage. As another classification according to differentiation potency of stem cells, stem cells can be divided into pluripotent, multipotent, and unipotent stem cells.

Adult stem cells can be classified as multipotent or unipotent stem cells. As representative adult stem cells, there are mesenchymal stem cells (MSCs) and hematopoietic stem cells (HSCs). It is known that mesenchymal stem cells differentiate into chondrocytes, osteoblasts, adipocytes, myocytes, and neurons, and that hematopoietic stem cells mainly differentiate into blood cells in blood, such as erythrocytes, leukocytes, or platelets.

Meanwhile, pluripotent stem cells refer to stem cells with multipotency which can differentiate into all three germ layers constituting the body, thereby capable of differentiating into every cell or organ tissue of human bodies. Generally, embryonic stem cells correspond thereto. Human embryonic stem cells raise many ethical concerns, because they are created from embryos that may develop into human beings. However, embryonic stem cells are known as having excellent cell proliferation and differentiation potency, compared with adult stem cells. Adult stem cells cause less ethical issues, because they can be obtained from bone marrow, blood, brain, skin, and the like. However, adult stem cells have limited differentiation potency, compared with embryonic stem cells.

As a solution for overcoming these problems, various techniques have been attempted to produce customized pluripotent stem cells similar to embryonic stem cells by dedifferentiating cells derived from adult stem cells. Representative techniques include fusion with ES cell, somatic cell nuclear transfer, reprogramming by gene factor, and the like. According to fusion with ES cell, induced cells have two further pairs of genes, and this causes a problem in terms of stability of cells. Somatic cell nuclear transfer requires a large number of ovums and has very low efficiency, which are disadvantages. Reprogramming by gene factor is a technique of using viruses including oncogenes by inserting specific genes, to induce dedifferentiation, and this technique has a high risk of cancer occurrence and is disadvantageous in possibility of development of cell therapy products due to low efficiency and difficulty in terms of methods.

In order to obtain pluripotent stem cells successfully and abundantly, medium compositions in the stage of culturing isolated umbilical cord-derived mononuclear cells is very important. Thus, there is a demand for studies for preparing pluripotent stem cells with a much more amount and in a higher efficient induction method.

The matters provided in the above background art are only intended to help better understand the background of the present invention. It should not be construed, however, that the present invention falls under the related art already known to a person skilled in the art.

DISCLOSURE

Technical Problem

The present inventors attempted to seek a method for inducing pluripotent stem cells with high efficiency for developing cell therapy products with high safety and production efficiency in practice. As a result, the present inventors found that when *Ecklonia cava* extracts, safe natural extracts, are added to cell culture media, induced pluripotent stem cells can be produced safely and highly efficiently, using mesenchymal stem cells, and thus completed the present invention.

As such, it is an object of the present invention to provide a medium composition containing an *Ecklonia cava* extract for dedifferentiating a mesenchymal stem cell into an induced pluripotent stem cell.

It is another object of the present invention to provide a method for producing an induced pluripotent stem cell, including dedifferentiating a mesenchymal stem cell into an induced pluripotent stem cell in a medium comprising an *Ecklonia cava* extract.

It is yet another object of the present invention to provide an induced pluripotent stem cell produced by the above method.

It is yet another object of the present invention to provide a composition comprising the induced pluripotent stem cell for treating a cell.

Other objects and advantages of the present invention can be more clearly understood by the following detailed description of the invention, claims and drawings.

Technical Solution

According to an embodiment of the present invention, there is provided a medium composition comprising an *Ecklonia cava* extract for dedifferentiating a mesenchymal stem cell into an induced pluripotent stem cell.

The present inventors attempt to seek a method for inducing pluripotent stem cells highly efficiently for developing cell therapy products with high safety and production efficiency in practice, without raising ethical concerns about the destruction of embryos. As a result, the present inventors found that when *Ecklonia cava* extracts, safe natural extracts, are added to cell culture media, induced pluripotent stem cells can be produced with surprisingly high efficiency.

*Ecklonia cava*, as an active ingredient contained in the medium composition of the present invention, is a perennial brown marine alga belonging to the order Laminariales, the family Lessoniaceae, mainly occurring in the southern coast, and the ocean off Jeju-do and Ulleung-do, Korea, is mainly fed by abalones, conches, and the like, and is used as main raw materials for preparing an alginic acid, iodine, or potassium, or as foods.

The *Ecklonia cava* extract used in the present invention may be extracted using water or an organic solvent, such as (a) an anhydrous or hydrous lower alcohol having 1 to 4 carbon atoms (methanol, ethanol, propanol, butanol, normal-propanol, isopropanol and normal-butanol, and the like), (b) a mixed solvent of the lower alcohol and water, (c) acetone, (d) ethyl acetate, (e) chloroform, (f) 1,3-butylene glycol, (g) hexane, (h) diethyl ether, and the like, and preferably a mixed solvent of methanol or ethanol with water. In the case of extracting using the mixed solvent, methanol or ethanol is preferably contained in an amount of 50 to 80 v/v %.

Recently, cases applying the *Ecklonia cava* extract to a skin composition, such as cosmetics, increase (See, Korean Patent Application Laid-open Nos. 2013-0017159, 2012-0040488, 2010-0097293, and the like). However, there is no case where the *Ecklonia cava* extract develops into a medium for induction of a pluripotent stem cell.

As used herein, the term "embryonic stem cell" refers to a cell having pluripotency, isolated and cultured from the inner cell mass of a blastocyst, an early-stage development after fertilization. As used herein, the term "pluripotent stem cell" refers to a stem cell having pluripotency, capable of differentiating into all three germ layers, i.e., the endoderm, mesoderm, and ectoderm, which constitute the body.

As used herein, the term "differentiation" refers to a process by which cells become more specialized in structure or function during cell growth through division and proliferation, i.e., a process by which cells, tissues, and the like of a living body change in shape or function in order to perform the given task.

As used herein, the term "cell therapy product," which is a pharmaceutical used for the purpose of treatment, diagnosis, and prevention with cells and tissues prepared from human beings by isolation, culture, and specific manipulation, refers to a pharmaceutical used for the purpose of treatment, diagnosis, and prevention through a series of actions, such as changing biological properties of cells by proliferating or selecting allogeneic or xenogeneic cells in vitro, or by other ways, in order to restore functions of cells or tissues. The cell therapy product is broadly classified as a somatic cell therapy product and a stem cell therapy product, according to the degree of differentiation of cell. The present invention particularly relates to the stem cell therapy product.

The mesenchymal stem cell of the present invention is a cell isolated from an embryonic stem cell or an adult stem cell derived from mammals, preferably an umbilical cord-derived mesenchymal stem cell, and more preferably a human umbilical cord-derived mesenchymal stem cell. The stem cell can be obtained by collecting an umbilical cord connecting the fetus and placenta in human bodies. The mesenchymal stem cell from the umbilical cord can be collected using various methods. For example, a solution containing a mononuclear cell can be obtained by collecting the umbilical cord from human bodies, washing the collected umbilical cord using DPBS until blood no longer comes out, cutting the washed umbilical cord using a surgical blade, and subjecting it to incubation at 37° C.

As used herein, the term "medium" refers to a mixture for in vitro culture or differentiation of a cell, such as stem cell and the like, containing elements essential for growth and proliferation of the cell, such as sugars, amino acids, various nutriments, serums, growth factors, minerals, and the like.

Various media are sold on the market in the art, and a medium may be artificially produced to be used. Media on the market may include Dulbecco's Modified Eagle's Medium (DMEM), Minimal Essential Medium (MEM), Basal Medium Eagle (BME), RPMI 1640, F-10, F-12, DMEM F-12, α-Minimal Essential Medium (α-MEM), Glasgow's Minimal Essential Medium (G-MEM), Iscove's Modified Dulbecco's Medium (IMPM), AMNIOMAX complete Medium (Gibco, New York, USA), AMNIOMAX complete Medium (AMNIOMAX and AMNIOMAX II are formulated and qualified for the in vitro propagation of primary culture of human amniotic fluid cells and chorionic villus samples for use in prenatal diagnostic testing (AMNIOMAX II includes gentamicin and L-glutamine)—Gibco, New York, USA), CHANG Medium (a media for human amniotic fluid cells that contains gentamicin) and MESENCULT-XF Medium (a standardized, xeno-free, serum free medium for human mesenchymal stem and progenitor cells (MSCs)—STEMCELL Technologies, Vancouver, Canada), and the like. These media, as well as media that may be artificially produced, may be used as a basal medium contained in the medium composition of the present invention.

A serum component (e.g., Fetal Bovine Serum (FBS)), an antibiotic (e.g., penicillin, streptomycin), and the like, which are typically added, may be added to the basal medium. The concentrations of the serum component or antibiotic component contained in the basal medium may vary within the range that can achieve the effect of the present invention, and preferably 10% FBS, 100 unit/mL penicillin, 50 µg/mL streptomycin, and the like may be added.

Also, the medium of the present invention may further contain a nutrient mixture. The nutrient mixture, a mixture including various amino acids, vitamins, mineral salts, and the like, which are generally used in cell culture, may be prepared by mixing the amino acids, vitamins, mineral salts, and the like, or a commercially prepared nutrient mixture may be used. Examples of commercially produced nutrient mixtures may include, but are not limited to, M199, MCDB110, MCDB202, MCDB302, and the like.

Also, the medium of the present invention may further contain energy water for the induction and stabilization of pluripotent stem cells. The energy water may be contained preferably in an amount of 0.01 to 10 v/v %, and more preferably in an amount of 0.05 to 0.5 v/v %.

The medium composition of the present invention can be achieved by adding the *Ecklonia cava* extract to the basal medium, as a medium specific for the induction of pluripotent stem cells, and may include the *Ecklonia cava* extract preferably in a concentration of 1 to 1,000 µg/mL, and more preferably in a concentration of 100 to 400 µg/mL, with respect to the total medium composition.

According to another aspect of the present invention, there is provided a method for producing an induced pluripotent stem cell, including adding an *Ecklonia cava* extract to a cell culture medium; and dedifferentiating a mesenchymal stem cell into an induced pluripotent stem cell in the medium.

According to an embodiment of the present invention, unlike the case of using DMEM F-12 medium alone, when using the medium composition containing the *Ecklonia cava* extract of the present invention, pluripotent stem cell colonies were formed on Days 8 to 10 (FIGS. 2 to 5).

According to another aspect of the present invention, the present invention provides an induced pluripotent stem cell prepared by the above production method.

The induced pluripotent stem cell of the present invention has the same differentiation potency as the embryonic stem cell, and has almost the same cell shape as the embryonic stem cell. According to an embodiment of the present invention, upon investigation of expression of genes (Nanog, Oct4, Sox-2, Klf) and protein (SSEA4) specific for the embryonic stem cell, it was confirmed that the genes and protein are expressed in the pluripotent stem cell induced by the present invention, in the same manner as in the embryonic stem cell (FIG. 4).

According to another aspect of the present invention, the present invention provides a composition for treating a cell containing the induced pluripotent stem cell produced by the above method.

The induced pluripotent stem cell of the present invention has the same pluripotency as the embryonic stem cell. According to an embodiment of the present invention, it was confirmed that the induced pluripotent stem cell of the present invention has pluripotency capable of differentiating into the endoderm, mesoderm, and ectoderm (FIG. 5).

Thus, the induced pluripotent stem cell of the present invention may be used as an effective cell therapy product.

The composition of the present invention may be injected via any administration routes, specifically, via intraperitoneal or intrathoracic administration, subcutaneous administration, intravenous or intraarterial administration, intramuscular administration, topical administration by injection, and the like.

According to the present invention, the composition may be administered in the form of injection, suspension, emulsion, and the like, according to a general method, and the composition may be suspended in an adjuvant, such as complete Freund's adjuvant or administered with a substance having an adjuvant activity, such as BCG, if necessary. The composition may be sterilized, or include an adjuvant, such as a stabilizer, a wettable powder or emulsifying promoter, or a salt or buffer for osmotic control, and other therapeutically useful substances. The composition may be produced according to a general mixing, granulating or coating method. The composition for treating a cell according to the present invention may contain a pharmaceutically acceptable carrier or additive, and may include a diluent (e.g., dextrose, sorbitol, cellulose, glycine, lactose, sucrose, mannitol), a binder (e.g., magnesium aluminum silicate, starch paste, tragacanth, sodium carboxymethylcellulose), a disintegrant (e.g., starch, agar, alginic acid or its sodium salt) or a boiling mixture and/or an absorbent, a sweetener, a flavor, and a colorant, in addition to active ingredients.

The composition for treating a cell according to the present invention may be applied to arthritis, neurological diseases, endocrine diseases, liver diseases, and the like, and might be used as an allogeneic cell therapy product for human beings later, according to clinical test results on human beings.

Advantageous Effects

The characteristics and advantages of the present invention are summarized as follows:

(i) The present invention provides a medium composition containing an *Ecklonia cava* extract for dedifferentiating an induced pluripotent stem cell.

(ii) Also, the present invention provides a method for producing an induced pluripotent stem cell using the medium composition.

(iii) The use of the medium composition according to the present invention allows an efficient production of an induced pluripotent stem cell using a mesenchymal stem cell, and the produced pluripotent stem cell can be useful as a cell therapy product, because it is capable of differentiating into a variety of cells.

BEST MODE FOR CARRYING OUT THE INVENTION

Figure 1:
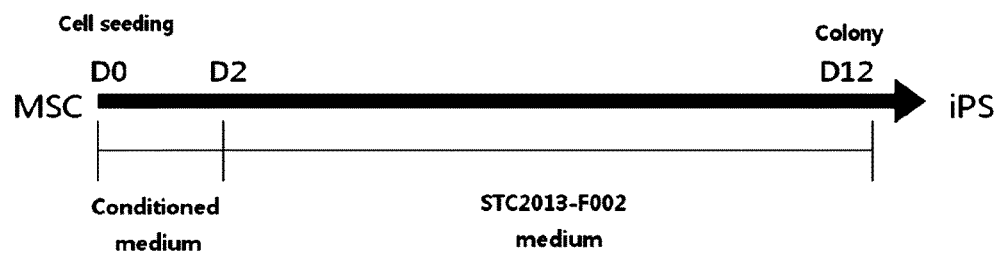
FIG. 1 is a view illustrating that when a mesenchymal stem cell is cultured in an *Ecklonia cava* extract medium, a pluripotent stem cell almost the same as an embryonic stem cell is induced.

Hereinafter, the present invention will be described in detail with reference to examples. The examples are only intended to specifically describe the present invention, and it will be apparent to a person skilled in the art that the scope of the present invention is not limited to these examples, according to the gist of the present invention.

EXAMPLES

Example 1: Preparation of *Ecklonia cava* Extract

Herbal medicine samples used in experiments were purchased from Jeju-do and used in experiments after having experts' accurate appraisal. 100 g of dried herbal medicine samples were put into 1 L of 70% methanol, extracted under reflux for 16 hours, and filtered using a filter paper. The filtrate was concentrated in a rotary evaporator under reduced pressure and freeze-dried immediately.

Example 2: Isolation of Mesenchymal Stem Cell from Human Umbilical Cord and Culture Thereof Example 2-1: Collection of Human Umbilical Cord Umbilical cord tissues are collected right after delivery. Before samples are transferred to the laboratory, the umbilical cord tissues are rinsed thoroughly, and transferred immediately to 500 mL of a sterilized glass bottle containing F-12 medium to which a transport medium (50 IU/mL of penicillin, 50 μg/mL of streptomycin (purchased from Invitrogen)) is added. In the laboratory, extraction of stem cells is performed in a flow hood, Class 100, under sterile conditions. Samples are first transferred to a stainless steel sterilization container. The umbilical cord tissue samples are washed several times by PBS, and they are cut into 2 cm long and transferred to cell culture dishes having a diameter of 10 cm. Here, the samples are additionally washed and subjected to anti-infective treatment with 70% ethanol, and washed several times with PBS to which an antibiotic mixture (50 IU/mL of penicillin, 50 μg/mL of streptomycin (purchased from Invitrogen)) is added, until the solution is clean.

Example 2-2: Isolation of Stem Cell from Human Umbilical Cord and Culture Thereof In order to isolate Wharton's jelly (base of umbilical cord) from blood vessels and other internal elements of umbilical cord, the umbilical cord is first incised. After removing blood vessels, the isolated Wharton's jelly is cut into small pieces (0.5 cm×0.5 cm) in order to extract cells. Explant is performed by putting the pieces of the umbilical cord Wharton's jelly into different tissue culture dishes with cell culture conditions suitable for extraction of epithelial stem cells or mesenchymal stem cells.

In order to isolate/culture mesenchymal stem cells, the explanted tissues are immerged in 5 mL of Dulbecco's modified eagle media (DMEM) F-12 (Gibco) supplemented with 10% fetal bovine serum (FBS, Hyclone), 10% FBS, 100 unit/mL of penicillin, and 50 μg/mL of streptomycin, and maintained in a $CO_2$ incubator at 37° C. The media are replaced every three or four days. The outgrowth of cells is monitored with an optical microscope. The outgrowing cells are treated with trypsin (0.125% trypsin/0.05% EDTA) for further expansion and frozen storage (using DMEM/10% FBS).

The media are replaced every three or four days. The outgrowth of cells from the explanted tissues is monitored with an optical microscope.

In order to extract mesenchymal stem cells, pellets of cells are resuspended and counted in media DMEM F-12 (Gibco), 10% FBS, 100 unit/mL of penicillin, and 50 μg/mL of streptomycin, and are inoculated into tissue culture dishes having a diameter of 10 cm in a density of $1 \times 10^6$ cell/dish. The media are replaced every three or four days. The growth of cells and formation of clones are monitored with an optical microscope. In about 90% confluence, cells are sub-cultured as described above.

Experimental Example 1: Induction of Pluripotent Stem Cell from Mesenchymal Stem Cell

Experimental Example 1-1: Preparation of Pluripotent Stem Cell of Human-Derived Mesenchymal Stem Cell Depending on Concentrations of *Ecklonia cava* Extract In an experiment for inducing pluripotent stem cells from human umbilical cord-derived stem cells depending on the concentrations of Jeju *Ecklonia cava* extracts, for a control group, dedicated media to MSC, DMEM F-12 (Gibco), 10% FBS, 100 unit/mL of penicillin, and 50 μg/mL of streptomycin were used as basal media. For an experimental group, using human umbilical cord-derived mesenchymal stem cells subjected to subcultures three times, Jeju *Ecklonia cava* extracts in the concentrations of 1 μg/mL, 10 μg/mL, 100 μg/mL, 200 μg/mL, 400 μg/mL, 800 μg/mL, and 1000 μg/mL, and 0.1 v/v % of energy water (purified deionized water containing $SiO_2$, $Al_2O_3$, $TiO_3$, $Fe_2O_3$, $CaO$, $Na_2O$, $K_2O$, and $LiO$, STC Nara Co., Ltd) were added to media (FIG. 1). The human umbilical cord-derived mesenchymal stem cells were isolated and $1 \times 10^4$ washed mononuclear cells were inoculated to 6-well plates (dishes) and maintained at 37° C. and 5% $CO_2$ to be cultured.

Figure 2:
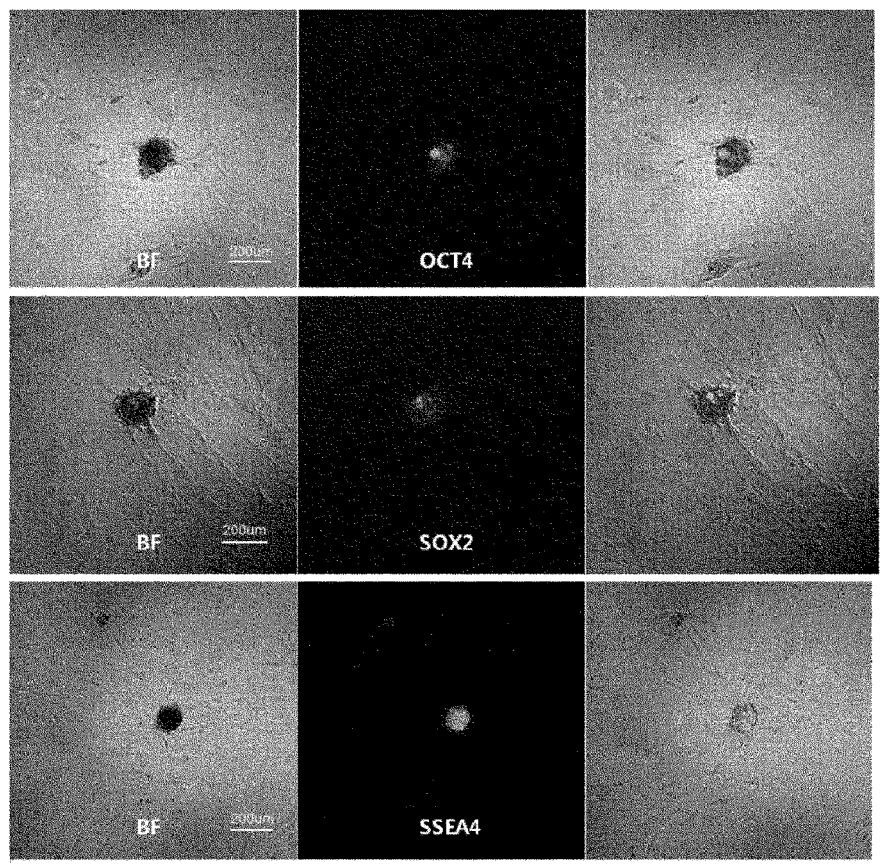
FIG. 2 confirms that a pluripotent stem cell induced according to the method of the present invention is a pluripotent stem cell, by using specific protein expression.

With respect to the pluripotent stem cells induced according to the method of the present invention, the expression of proteins OCT4, SOX2, and stage-specific embryonic antigen4 (SSEA4) specific for embryonic stem cells was analyzed using antibodies thereagainst through immunochemistry staining. As a process for straining, the cells were fixed with 4% paraformaldehyde, washed with PBS, and blocked with 1% BSA solution. Then, primary antibodies against OCT4, SOX3, and SSEA4 were treated and reacted at 4° C. for 18 hours and washed with PBS, and secondary antibodies attaching fluorescence (FITC) against the primary antibodies were treated and reacted at room temperature for 1 hour. After washing with PBS, the protein expression was analyzed using a confocal microscope, and the results are shown in FIG. 2. BF indicates bright field, the second figure indicates the staining results of each protein expression, and the third figure combines the two figures (FIG. 2).

Figure 3:
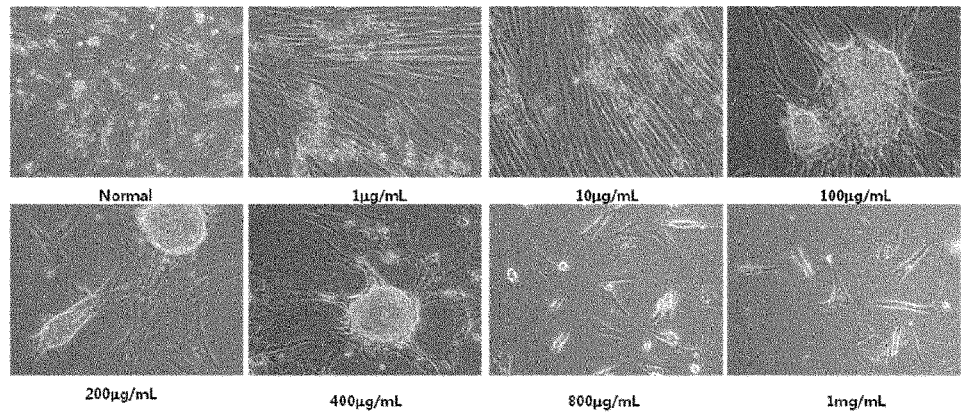
FIG. 3 illustrates the formation of pluripotent stem cell colonies induced depending on concentrations of an *Ecklonia cava* extract, according to the method of the present invention.

As a result, in the experimental group, it was observed that colonies were formed after 10 days only when the concentration of Jeju *Ecklonia cava* extract is between 100 and 400 μg/mL (FIG. 3). Further, markers specific for pluripotent stem cells, OCT4, SOX2, and SSEA4, were stained only in colonies, and were confirmed to be pluripotent stem cells.

Figure 4:
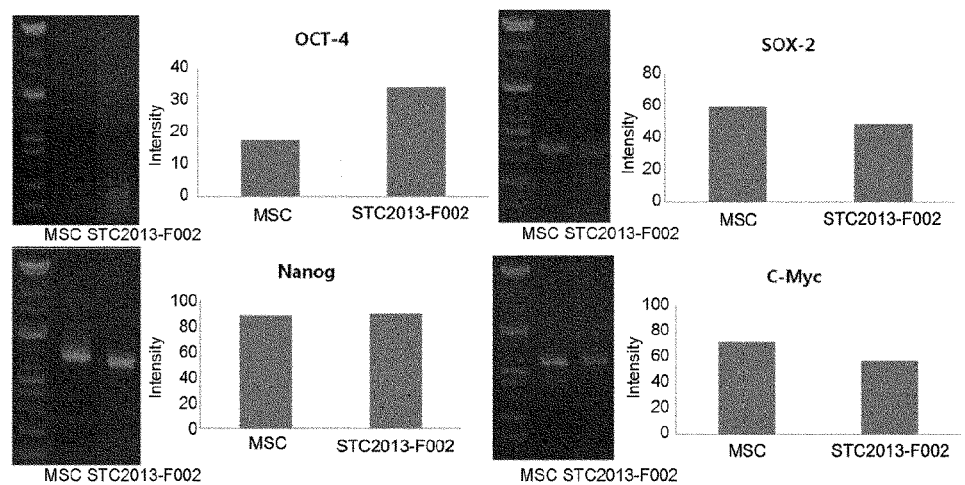
FIG. 4 illustrates gene expressions of a pluripotent stem cell induced according to the method of the present invention.

Experimental Example 1-2: Gene Comparison Analysis of Pluripotent Stem Cell Colonies were cut out from the pluripotent stem cells prepared in Example 2-1 above, using 200 μl pipette, while observing the pluripotent stem cells through a microscope, and then total RNA was isolated using TRIzol reagent (manufactured by Invitrogen). cDNA was synthesized using reverse transcription-polymerase chain reaction (RT-PCR), and then PCR was proceeded using primers specific for OCT4, Sox-2, Nanog, c-Myc, and the control gene, glyceraldehyde 3-phosphate dehydrogenase (GAPDH). Nanog, OCT4, and Sox-2 are characteristic genes shown in embryonic stem cells, and c-Myc is a non-specific gene that may be shown positive in both embryonic stem cells and adult stem cells. PCR products were analyzed using agarose gel electrophoresis, and the results confirming the expression of the genes are shown in FIG. 4. According to FIG. 4, the expression of OCT4, which is a characteristic gene of pluripotent stem cells, is low in mesenchymal stem cells which did not undergo an induction process, whereas the expression of the characteristic genes was significantly high in pluripotent stem cells (STC2013-F002) induced by the method of the present invention. SOX2 and Nanog, stem cell genes, were expressed at a similar level, and c-Myc, a non-specific gene, was expressed at a lower level in cells (STC2013-F002) which underwent an induction process, than in cells which did not undergo an induction process.

Experimental Example 2: Confirmation of Pluripotent Stem Cell by Teratoma Test In order to analyze differentiation potency in vivo of pluripotent stem cells induced by the method of the present invention, undifferentiated pluripotent stem cell colonies which were cultured on support cells, were treated with trypsin-EDTA on day 5 after culture and cut out therefrom, then put into collagenase, and maintained in an incubator for 30 minutes. The undifferentiated pluripotent stem cells were collected, and $1 \times 10^6$ cells were administered via a subcutaneous injection to mice with severe combined immune deficiency (SCID). Formed teratomas were harvested after 4 weeks and fixed with 4% paraformaldehyde to be subjected to typical paraffin embedding. Tissues were cut into 10 μm thick and stained with hematoxylin and eosin.

Figure 5:
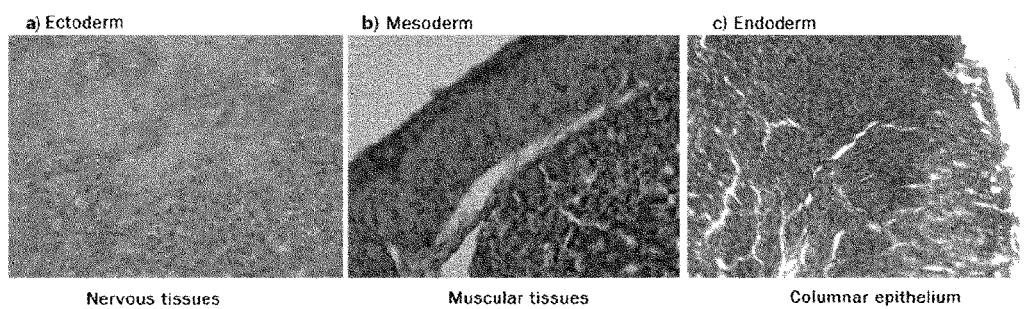
FIG. 5 illustrates test results of differentiation potency in vivo of a pluripotent stem cell induced according to the method of the present invention.

According to FIG. 5, teratomas were macroscopically formed in a place where induced pluripotent stem cells produced by the method of the present invention were injected. Specifically, it was demonstrated that histologically, teratomas were formed which are capable of differentiating into nervous tissues derived from the ectoderm (FIG. 5a), muscular tissues derived from the mesoderm (FIG. 5b), stomach tissues derived from the endoderm (columnar epithelium, FIG. 5c), and the like. From the experiments, it can be confirmed that the cells induced by the method of the present invention have pluripotency that is practically the same as embryonic stem cells in vivo, i.e., pluripotency capable of differentiating into the ectoderm, mesoderm, and endoderm.

Particular parts of the present invention were described in detail as above. It will be apparent to a person having ordinary knowledge in the art that these specific descriptions are only desirable embodiments, and that the scope of the present invention is not limited to these embodiments. Thus, the substantial scope of the present invention should be construed as being defined by attached claims and their equivalents.

What is claimed is:

1. A method for producing an induced pluripotent stem cell, the method comprising:

adding an *Ecklonia cava* extract to a cell culture medium; and dedifferentiating a mesenchymal stem cell into an induced pluripotent stem cell in the medium.

2. The method of claim 1 wherein the cell culture medium comprises Dulbecco's Modified Eagle's Medium (DMEM), Minimal Essential Medium (MEM), Basal Medium Eagle (BME), RPMI 1640, F-10, F-12, DMEM-F12, α-Minimal Essential Medium (α-MEM), Glasgow's Minimal Essential Medium (G-MEM), Iscove's Modified Dulbecco's Medium (IMDM), McCoy's 5A Medium, a media for in vitro propagation of primary cultures of human amniotic fluid cells and chorionic villus samples, a media for in vitro propagation of primary cultures of human amniotic fluid cells and chorionic villus samples that includes gentamicin and L-glutamine, a media for human amniotic fluid cells that contains gentamicin, or a defined xeno-free media for human mesenchymal stem cells.

3. The method of claim 1 wherein the *Ecklonia cava* extract is comprised in the medium in an amount of 100 to 400 μg/mL with respect to the medium composition.

4. The method of claim 1, wherein the medium further comprises 0.01 to 10 v/v % of purified deionized water containing $SiO_2$, $Al_2O_3$, $TiO_3$, $Fe_2O_3$, CaO, $Na_2O$, $K_2O$, and LiO.

* * * * *